United States Patent [19]

Vassiliades

[11] Patent Number: 5,075,278

[45] Date of Patent: Dec. 24, 1991

[54] CHROMOGENIC COPY SYSTEMS AND METHODS

[76] Inventor: Anthony E. Vassiliades, 8738 Tanager Woods Dr., Cincinnati, Ohio 45249

[21] Appl. No.: 665,912

[22] Filed: Mar. 4, 1991

Related U.S. Application Data

[63] Continuation of Ser. No. 352,107, Sep. 12, 1988, abandoned, which is a continuation-in-part of Ser. No. 101,593, Sep. 28, 1987, abandoned, which is a continuation-in-part of Ser. No. 76,326, Jul. 22, 1987, abandoned.

[51] Int. Cl.$^5$ .................. B41M 5/155; C09D 11/00
[52] U.S. Cl. ........................... 503/210; 106/21; 427/150; 503/211; 503/212; 503/216; 503/225
[58] Field of Search .............. 106/21; 427/150; 503/210-212, 216, 225

[56] References Cited

U.S. PATENT DOCUMENTS 3,934,070  1/1976  Kimura et al. .................. 428/342

Primary Examiner—Bruce H. Hess

[57] ABSTRACT

A pressure-sensitive chromogenic copy system comprising a transfer sheet having on at least a portion of at least one surface thereof a color developer capable of reacting with a chromogen to form a color image, said color developer comprising a crude reaction medium resulting from reactants used to prepare a salicylate and also containing therein at least one metal compound of such salicylate, the resultant transfer sheet, color developer and process for making such color developer.

64 Claims, No Drawings

CHROMOGENIC COPY SYSTEMS AND METHODS

CROSS-REFERENCE TO RELATED APPLICATION

This application is a continuation of application Ser. No. 352,107 filed Sept. 12, 1988, now abandoned, which is a continuation-in-part of U.S. application Ser. No. 101,593 filed Sept. 28, 1987, now abandoned, which was in turn a continuation-in-part of U.S. application Ser. No. 076,326 filed July 22, 1987, now abandoned.

BACKGROUND OF THE INVENTION

The present invention relates to novel pressure-sensitive chromogenic copy systems and receptor sheets and transfer sheets therefor, as well as novel compositions for use as color developers.

The use of aromatic carboxylic acids in carbonless copying systems has been known in the art for a long time, and is described, among others, in U.S. Pat. Nos. 3,488,207, 3,682,680, 3,772,052, 3,871,900, 3,896,255, 3,900,215, 3,934,070, 3,983,292, 4,303,719, 4,374,671, 4,372,583, 4,559,242, and 4,631,204. The salicylates, their metallic compounds and other salicylate derivatives including oligomers of salicylates and their metal compounds, appear to offer the best overall properties as image developers in carbonless systems. The rather complex manufacturing methods known to date for producing salicylates and the associated relatively high cost, however, has prevented any significant use of such materials in carbonless copy systems on a commercial basis.

It has now been discovered that a number of changes in the conventional production methods of salicylates can be made which changes result in a significant reduction of the manufacturing costs of these salicylates without diminishing their desired properties as color-developing materials in carbonless papers. These new processing methods are applicable to all the known syntheses reactions for manufacture of salicylates and salicylate derivatives, and can yield materials with attractive and competitive cost structure which can result in a widespread use of these compounds in the carbonless paper industry. Additionally, the new processing methods afford color developing materials which possess significantly improved properties (image intensity, speed of image formation, and image stability) over materials known in the prior art.

One of the commonly-used methods for producing salicylates is the well-known Kolbe-Schmitt reaction (Schmitt, J. Pract. Chem., [ii], 31,397 (1885)), whereby the sodium salt of a phenol is heated with carbon dioxide under pressure at a temperature of between 130-140° C. Another method for manufacturing salicylates is described by W. Meek and C. Fuschman in the Journal of Chemical and Engineering Data, (Vol. 14, No. 3, July 1969, p. 388) whereby carboxylation of substituted phenols is performed under atmospheric conditions and with the use of N,N'-dimethylamide solvents to produce substituted salicylates in superior yields.

Still another method for manufacturing salicylates of the present invention is the combination of the two aforementioned manufacturing methods, i.e., the use of solvents in combination with the use of pressurized environments of varying temperatures.

Irrespective of the manufacturing method used, the salicylates must be processed extensively; i.e., they must go through steps such as layer separation (if a solvent is used), purification (often repeated purification steps involving counter-current extractions), precipitation of the alkali salt of the salicylate to obtain the free acid by acidifying the aqueous layer containing the salicylate salt, filtration, and drying.

If the salicylate or salicylate derivative is to be used as a color developer, the carbonless system manufacturer must process the material further to incorporate it into a coating and apply it to the color-developing substrate. Such further processing by the carbonless manufacturer may involve steps such as grinding, dissolution, mixing with pigments and binders, and, optionally, the formation of a polyvalent metal salt of the salicylate.

All the aforementioned processing steps by the manufacturer of the salicylate and the manufacturer of the final carbonless product render the use of salicylate and salicylate derivatives economically unattractive.

SUMMARY OF THE INVENTION

It has now been surprisingly found that impure (crude) salicylic-containing compositions can be utilized without any purification as color-developing components in carbonless copy papers.

Briefly, the present invention comprises forming a salicylic derivative capable of reacting with a chromogen used in carbonless copy papers and, after formation of the crude reaction medium containing such salicylic component, reacting or otherwise combining the crude suspension with a hydrogen-donating compound or a metallic compound, preferably a lithium or a multivalent metallic compound of a metal selected from Groups IIIA through IVB of the Periodic Table, or mixtures thereof to form a metal compound of the salicylate.

The invention also comprises carbonless copy systems utilizing such products produced in accordance with the teachings of this invention; e.g., the products produced from the salicylic components, as well as transfer sheets and receptor sheets useful in carbonless papers, as well as the resultant color-developer compositions.

DETAILED DESCRIPTION

As used herein, the phrase "metal compound of the salicylate" means salts, complexes, adducts, esters, mixtures, and all other products resulting from combining the salicylates with the noted metal compounds.

Also the term "crude" means that the reaction mixture resulting from the carboxylation step is not treated to the extent necessary to obtain a salicylic component in completely pure form. Partial purification such as washing and/or distillation and/or extraction may be employed to reduce some of the impurities present. For instance, the content of unreacted phenol may be lowered to no less than about 10%, more usually no less than 15 to 20% by weight of the reaction mixture. However, it has also been found that the reaction mixture from the carboxylation reaction containing 30% or more unreacted phenol can be used without any purification.

The particular salicylate used is of little relevance. It can, for example, either be a salicylic acid, or oligomeric or polymeric salicylate or thiosalicylate, or any other salicylate which has been or can be used as a color developer in carbonless copy systems. Examples have been noted above with reference to certain patents. Preferably, salicylic acid and alkylated, cycloalkylated, or arylated salicylates are used. Salicylates with $C_1$ to $C_{20}$ alkyl groups are used; $C_2$ to $C_{12}$ alkylated salicylates being especially preferred with octyl and nonyl salicylates being exemplary. As to the arylated salicylates, any phenyl or cyclohexyl salicylic acid can be used.

Of significance and importance is the proper processing of the material during its manufacture.

In one aspect of this invention relating to the manufacture of salicylates by the well-known reaction between substituted or unsubstituted phenols with carbon dioxide in water under pressure, the entire reaction mixture after the reaction is completed is treated in accordance with the present invention to produce the desired salicylate moiety. The thus treated crude mixture contains the desired salicylate moiety as well as up to about 80% by weight of unreacted phenol, carbonates (primarily bicarbonates) and other impurities. After the reaction between the phenol and carbon dioxide has been completed, the pH of the crude aqueous medium is raised to between about pH 7.5 to 12.5 with an alkali such as aqueous ammonia, LiOH, NaOH, KOH, or combinations of aqueous amonia with LiOH or with other water soluble hydroxides; aqueous ammonia or combinations of aqueous ammonia with other alkalis has been found to be the preferred way of adjusting the pH of the coating dispersions containing the crude salicylates of this invention.

Following the adjustment of the pH of the crude aqueous medium, a polyvalent metallic compound selected from Groups IIIA through IVB of the Periodic Table may be added to form the desired metal compound of the salicylate. The use of lithium alone in an amount stoichiometric to the particular salicylic acid in the crude mixture or in an amount less than stoichiometric and using aqueous ammonia to reach stoichiometry or beyond can obviate the use of polyvalent metallic compounds.

Further, it has been unexpectedly found that the careful adjustment of the pH of the final coating dispersion with a hydrogen-donating compound such as an organic or inorganic acid; e.g., hydrochloric, acetic, sulfuric, citric, maleic, glyoxylic, glycolic, and the like and mixtures thereof can also obviate the use of polyvalent metal compounds.

Another unexpected finding of this invention is that controlling the pH of the coating dispersions containing salicylates or salicylate derivatives, made in accordance with the processes of this invention, by the use of aqueous ammonia and permanent alkalis, along with the use of mineral inorganic acids to effect a pH of the dried CF coated surface of between 5.0 and 8.0, and preferably between 5.5 and 7.5, can offer the best image properties of the salicylates as color developers. The preferred mode of this invention, however, is the use of polyvalent metal compounds along with the careful pH adjustments of the coating dispersions and coated surfaces. Preferred polyvalent metals added are zinc, nickel, cadmium, titanium, aluminum, tin, magnesium, and manganese and the like, and mixtures thereof with zinc being especially preferred. It is possible to use a mixture of polyvalent metals and the monovalent lithium and/or hydrogen compounds. Dependent upon the particular salicylate, the metal compound used, and the quantity thereof which is added, a precipitate may form, but such precipitate as well as the remaining portions of the aqueous solution containing the other materials such as noted unreacted phenol, bicarbonates, and the like or the entire solution, if no precipitate is formed, can be easily and directly formulated as hereinafter set forth into a color-developing coating.

The mechanism by which the presence of metallic compounds potentiate the image-forming and image-stabilizing properties of the salicylate compounds is not well understood to date. It has been found, however, during the course of this invention that the nature, i.e., ionizable (salt), or nonionizable (pigments, etc.), of the metallic compound used to form the final salicylate color developer does not appear critical; this point is easily exemplified in Table I, where various salicylates, combined with different metallic compounds of varying nature such as salts, pigments, and esters, exhibit essentially no difference in their ability to affect the intensity, or the light stability of the final image formed.

The color-developing coating is prepared by admixing the impure salicylate mixture with conventional pigments such as clays, carbonates and the like and/or conventional adhesives or binders such as natural or modified starches, latexes, partially or fully hydrolyzed polyvinyl alcohols, proteins, gums, and the like conventionally used in forming carbonless copy paper; all being added in their usual amounts for their usual effect. Other conventional additives such as pigment dispersants and coating lubricants can also be used.

The main function of the conventionally used pigments in preparing coated front (CF) formulations, is to "extend" or "spread out" the principal color-developing material for a more efficient use. In this invention, the nature of the extending pigment is inconsequential; calcium carbonate, various types of clays, or combinations of calcium carbonate and clays have been used as extending pigments in formulating the impure salicylates of this invention, without any apparent influence in the functional properties of the CFs containing the salicylates noted herein as color developers. This is demonstrated in Table II, where the same salicylate moiety is formulated with different extending pigments without any evident loss in functional properties.

A generally accepted indicator of the efficiency of a color developing material in carbonless CF papers is the amount of the color developer used relative to the amount of the extending pigment, usually expressed as a percent by weight of the color developer on the weight of the pigment. It has been surprisingly found during the development of this invention that only relatively small amounts of the salicylates are required to give superior results, i.e., speed of image formation and image intensity and stability, when the salicylates are manufactured and processed in accordance with the modes described herein. For example, 4% to 10% by weight of the salicylates of the present invention on the weight of the pigment is sufficient to produce superior image intensities and stabilities compared to color-developing materials heretofore described in the prior art [U.S. Pat. Nos. 3,934,070, 4,051,303, 4,147,830, 4,159,208 and others] and reported to be used at between 30% and 1000% of the weight of the color developer on the weight of the pigment.

The final mixture is applied in the conventional manner as by conventional paper coaters, such as an air knife, gate roll, blade, reverse roll, and the like in the usual thickness to substrates conventionally used for forming carbonless copy paper (usually paper) to form the color-developing part (receptor or transfer sheet) of a carbonless pressure-sensitive chromogenic copy system. Alternatively, the coating noted can be mixed with a solution of leuco dyes containing microcapsules and applied to a single surface to form a "self-contained" type of carbonless system.

If the manufacturing method used to produce the salicylate involves the use of a solvent, the salicylate formed is usually extracted from the solvent by the addition of sufficient amounts of water and unreacted or uncarboxylated phenols usually stay mainly in the solvent layer and do not interfere with the processing of the water layer. The water layer in addition to the desired salicylate usually contains up to about 5% to 6% by weight of solvent, up to 50% by weight or more of unreacted phenol, up to about 10% by weight of catalyst, and up to about 15% by weight of carbonates (primarily bicarbonates). Following the separation the water layer is treated in the manner described above to form the metal compound of a salicylate and color developer.

If an oligomeric or polymeric condensation product of the salicylate is the final desired color developer subsequent to the carboxylation reaction and layer separation, if one is required, as is conventional, the pH of the water layer is again adjusted to the alkaline side for the formation of oligomers or pH on the acid side for the formation of higher molecular weight polymers and the condensation agent, such as an aldehyde or the like, is added and the condensation reaction is allowed to proceed under time and temperature conditions suitable for the formation of the desired product. Such reaction conditions are conventional and described in the literature. At the completion of the condensation reaction the total solution is treated in the same manner as described above with respect to treating the reaction product resulting from reacting phenols with carbon dioxide. In the event that the layer separation is not totally complete any residual solvent that may be carried through to the water layer does not have any detrimental effect on either the reactive processes of the salicylate as color developers, nor on the behavior or properties of the final coating.

For effective color-developer use, the crude salicylate solution should contain at least about 5% to 25% by weight of the particular salicylate. This permits preparation of the color developer which preferably should contain at least about 1% by weight of salicylate, dependent upon the particular salicylate used. Ordinarily larger amounts are utilized to ensure color development, such as at least about 4% by weight.

The presence of varying amounts of impurities have no detrimental effect on, and in some cases even improve, the overall performance of the salicylates of this invention as color developers, as can be demonstrated by the results presented in Table II. To have a proper comparison, the ratios of all the components such as salicylate to pigment, pigment to binder, etc., were kept constant; only the amount of the impurities was varied. All intensity measurements were made using the same, commercially available capsule-coated CB (Coated Back) paper. Strips of CB paper were mated with CF paper, a constant pressure was applied to crush the microcapsules of the CB paper and produce the colored images on the CF surface. The instrument used to make the intensity measurements was a Brightimeter Micro S4-M Brightness, Opacity, and Color Tester. The L value on the Hunter L,a,b scale which the Brightimeter calculates was taken as a measure of the color intensity of the images. Since lower L values on the 0-100 scale mean higher image intensities, the Intensity values (I) presented in Tables I and II were calculated as 100-L.

To measure light resistance, the colored images were exposed for twenty hours to a General Electric cool white fluorescent bulb at a distance of six inches and the intensity of the image was compared before and after exposure. The % light resistance was calculated from the following formula:

$$\% \text{ Light Resistance} = \frac{(I \text{ Before} - I \text{ After})}{I \text{ Before}} \times 100$$

The invention will be further described in connection with the following examples and tables which are set forth for purposes of illustration only.

EXAMPLE 1

Thirty-five grams of xylene, 20.6 grams (0.1 mole) of p-octyl phenol, and 12.5 grams of a 45% aqueous solution of potassium hydroxide are charged into a suitable reactor equipped with a turbine-type agitator. The reaction mixture is heated to reflux, separating the water into a Dean-Starke trap; heating is continued until the mixture is dehydrated and the theoretical amount of water (8.7 g) has been collected. The reaction mixture is cooled to 120° C. under a nitrogen atmosphere, and 7.3 grams (0.1 mole) of dimethyl formamide are added; while maintaining the agitation and the temperature to between 125-130° C., 4.5 grams of carbon dioxide are added to the mixture through a subsurface gas inlet tube for approximately 30 to 60 minutes. The solution temperature of 125-130° C. is maintained for about one additional hour after the addition of the carbon dioxide has been completed. The reaction mixture is then cooled to about 90° C., 68-70 grams of water are added with thorough mixing for about 15 to 20 minutes, the mixing is stopped and the phase separation is allowed to occur. The lower layer (water phase) containing the potassium salt octyl salicylic acid product (about 20% by weight) as well as the impurities; primarily octyl phenol, xylene, dimethyl formamide, and potassium bicarbonate, is drained off into a suitable vessel equipped with an agitator, and the pH is raised to between 12 and 13 with an aqueous solution of concentrated ammonia. Fourteen grams of a 50% by weight aqueous solution of zinc chloride are added slowly and with agitation forming a precipitate; this precipitate remains stable over an indefinite period of time and over a wide range of temperatures.

The coating can be prepared by applying the crude solution containing the flocculant precipitate directly to a paper substrate at very low coating weights of about 1.5 to 2.2 g/m$^2$, after mixing with small amounts (10% to 15% by weight on a dry basis) of one or more binders such ethylated or oxidized starches, and/or small amounts (10% to 15% by weight) of a styrenebutadiene latex (Dow's latex-638), producing a receptor or color developer coated front (CF) part of a carbonless paper product. When the CF surface is mated with a coated back (CB) part of a carbonless form containing leuco dyes (usually in an encapsulated form) and localized pressure is applied, bright and intense images are formed instantaneously on the CF surface.

Alternatively, the solution containing the flocculant precipitate is formulated into a coating by the addition of 200 grams of calcium carbonate, 130 grams of a 20% aqueous solution of ethylated starch, and 30 grams of Dow's latex-638 (48% by weight aqueous solution) and applied to a paper substrate at low coating weights (2 to 3 g/m²). Images of the same high intensity, speed and brightness as those obtained from the nonpigmented formulation are obtained.

COMPARATIVE EXAMPLE 1a

Twenty-five grams of pure, conventionally produced octyl salicylic acid are dissolved in 100 grams of water with the aid of 12.5 grams of a 45% aqueous solution of potassium hydroxide. The pH of the solution is raised to between 12 and 13 using a concentrated solution of aqueous ammonia, mixed with 14 grams of a 50% aqueous solution of zinc chloride and formulated into coatings (with and without pigments) as described in Example 1 above. The properties of the images formed on the CF paper of this example are identical to the properties of the images produced on the CF of Example 1.

EXAMPLE 2

Example 1 is repeated, but the aqueous layer containing the octyl salicylic acid is drained off into a suitable vessel equipped with an agitator, 4 grams of an aqueous (37% by weight) formaldehyde solution are added and the reaction mixture is heated to between 85 and 90° C. and maintained at this temperature for 2 to 4 hours while maintaining the pH at between 8.5 and 9. At the end of this reaction, almost all of the formaldehyde has been consumed, and oligomers of the octyl salicylate have been formed. The crude oligomeric octyl salicylate reaction mass is treated in a similar manner to that described in Example 1; i.e., the pH is raised to between 12 and 13 with concentrated aqueous ammonia, and the zinc chloride solution is added to form the flocculant precipitate. Subsequently, the solution containing the flocculant precipitate is formulated into the coatings described in Example 1 and applied to a paper substrate in equivalent coating weights. The images produced on such CF surfaces possess properties similar to the images produced in Example 1, but in addition they exhibit improved stability to severe light exposures.

EXAMPLE 3

Example 1 is repeated, but the p-octyl phenol is replaced with equimolar quantities of p-tert.butyl phenol. Equivalent results are obtained.

EXAMPLE 4

Example 2 is repeated, but the water layer contains the p-tert.butyl salicylate produced in Example 3. The CF papers produced using the methods described in Example 1 exhibit equivalent properties.

EXAMPLE 5

Example 1 is repeated, but the p-octyl phenol is replaced with equimolar quantities of 2,4, ditertiary butyl phenol. The resultant material, 3,5, ditertiary butyl salicylate, and/or its metal salts, when used as the color developer in a CF coating exhibit properties equivalent to those obtained with the octyl salicylate-containing CF.

EXAMPLE 6

Example 1 is repeated up to the point of draining off the lower layer (water phase) containing the potassium salt of the salicylic acid product, except that the p-octyl phenol is replaced with equimolar quantities of phenol. The resultant salicylic acid salt contained in the water layer is reacted with 16 grams of aqueous formaldehyde solution (37% by weight) in the presence of 25 grams of 12N sulfuric acid solution at a temperature of 95 to 97° C. for one hour to produce a high molecular weight polymer of salicylic acid. The alkaline salt of this material was treated in a manner similar to that described in Example 1 to form the flocculant precipitate, and formulated into coatings according to the methods described in Example 1. The CF papers produced containing the material of this example exhibited properties similar to those of the CF produced in Example 1, but the images required substantially higher amount of time to develop full intensities.

EXAMPLE 7

Example 1 is repeated throughout, but the p-octyl phenol is replaced with equimolar quantities of 2-methyl, 3-isobutylthiophenol. The resultant product, 2-hydroxy-4-methyl-5-isobutylthiobenzoic acid and/or its metal salts, when used as the color developer in a CF coating exhibit properties equivalent to those obtained with the CF containing the octyl salicylate product.

EXAMPLE 8

Example 1 is repeated in its entirety, but the p-octyl phenol is replaced with equimolar quantities of p-t-butylthiophenol. The resultant product, 2-hydroxy -5-t-butylthiobenzoic acid and/or its metal salts, when used as the color developer in a CF coating, exhibit properties equivalent to those obtained with the CF containing the octyl salicylate product.

EXAMPLE 9

Twenty grams of an impure mixture of m-nonyl salicylic acid and nonyl phenol containing about 11 grams (55% of total mixture weight) of nonyl phenol and about 1-1.5 grams of potassium carbonate and xylene, are dissolved in 100 grams of water containing 1.5 dry grams of sodium hydroxide. While maintaining the solution under agitation, 5.8 grams of 50% by weight of an aqueous solution of zinc chloride are added and allowed to react, forming the zinc salt of the nonyl salicylic acid. Subsequently, 100 grams of a 72% by weight dispersion of calcium carbonate in water are added along with 17 grams of Dow's latex-620 (50% by weight) and 42 grams of a 20% by weight aqueous solution of ethylated starch, the pH of the dispersion is adjusted to about 9.5 with concentrated aqueous ammonium hydroxide solution (28% by weight), and the final coating is applied to a paper substrate at coating weights of between 3 and 5 g/m², producing a receptor or color developer coated front (CF) part of a carbonless product. When the CF surface is mated with a coated back (CB) of a carbonless form containing leuco dyes (usually in an encapsulated form) and localized pressure is applied, bright and intense images are formed instantaneously on the CF surface.

EXAMPLE 10

The process of Example 9 is repeated except that 1 gram of lithium hydroxide is substituted for the 1.5 grams of sodium hydroxide used therein and no zinc chloride is added. Equivalent results are obtained.

EXAMPLE 11

Twenty grams of an impure mixture of m-nonyl salicylic acid and nonyl phenol containing about 50% by weight nonyl salicylic acid, about 43-45% by weight nonyl phenol, and about 5-7% by weight of potassium carbonate and xylene, are dissolved in 90 grams of water containing 0.5 dry gram of sodium hydroxide, and 10 grams of concentrated aqueous ammonium hydroxide. While maintaining the solution under agitation, 15 grams of zinc oxide are thoroughly dispersed therein. Subsequently, 213 grams of a 72% by weight dispersion of calcium carbonate and kaolin clays in water are added along with 36 grams of Dow's latex-620 (50% solids by weight) and 92 grams of a 20% by weight aqueous solution of ethylated starch. The pH of the dispersion is adjusted to about 11 with a concentrated aqueous ammonium hydroxide solution (28% by weight), and applied onto a paper substrate at a coating weight of between 5 and 7 g/m$^2$ producing a receptor or color developer coated front (CF) part of a carbonless product. When the CF surface is mated with a coated back (CB) of a carbonless form containing encapsulated leuco dye and localized pressure is applied, bright and intense images are formed instantaneously on the CF surface.

EXAMPLE 12

The process of Example 9 is repeated except that the amount of zinc chloride solution is reduced to 4 grams. Equivalent results are obtained.

EXAMPLE 13

The process of Example 11 is repeated except that the amount of zinc oxide is reduced to 4 grams. Equivalent results are obtained.

EXAMPLE 14

The process of Example 9 is repeated except that the zinc chloride is replaced with 15 grams of an 18% by weight solution of zinc octoate in mineral spirits. Equivalent results are obtained.

EXAMPLE 15

The process of Example 11 is repeated except that the 213 grams of the calcium carbonate and kaolin clays dispersion are replaced with 213 grams of a 72% by weight dispersion of kaolin clays in water. Equivalent results are obtained.

EXAMPLE 16

The process of Example 11 is repeated except that the 213 grams of the calcium carbonate and kaolin clays dispersion are replaced with 213 grams of a 72% by weight dispersion of a 50-50 mixture of calcium carbonate and kaolin clays. Equivalent results are obtained.

EXAMPLE 17

The process of Example 9 is repeated except that the zinc chloride is replaced with 8 grams of a 12% by weight hydrochloric acid solution. Equivalent results are obtained.

EXAMPLES 18–25

Examples 9 through 16 are repeated except that the 20 grams of the impure mixture of nonyl salicylic acid are replaced with 13.5 grams of an impure mixture containing about 75% by weight nonyl salicylic acid, about 20 to 22% by weight of nonyl phenol, and about 3 to 5% by weight potassium carbonate and xylene. Equivalent results are obtained in all cases.

EXAMPLES 26 AND 27

The processes of Examples 9 and 11 are repeated except that the 20 grams of impure nonyl salicylic acid mixture are replaced with 10 grams of pure nonyl salicylic acid. Comparable results are obtained.

EXAMPLE 28

A self-contained carbonless system is prepared by the following procedure:

Microcapsules containing leuco color formers are manufactured according to the specifications of U.S. Pat. No. 4,586,060, as follows:

An oil solution comprising 90 grams of monoisopropylbiphenol, 3 grams of Hilton Davis' N-102 black leuco dye, 1 gram of Crystal Violet Lactone, 0.5 gram of benzoyl leuco methylene blue, 0.4 gram of Hilton Davis' Kopichem XIV leuco dye, and 5 grams of a hexamethylene di-isocyanate adduct (Mobay's Desmondur L-2291A) are emulsified with 100 grams of a 13% by weight aqueous solution of gelatin (Hudson Industries G-110). Emulsification is continued until an average particle size of between 5 and 5.5 microns are obtained and the solution is heated to 65° C. for about two hours. Subsequently, 10 grams of a 10% by weight polyvinyl alcohol (Airco's Vinol-205), 1 gram of toluene, and 1 gram of Desmondure L-2291A are added with agitation and the heating is continued at 65° C. for an additional two hours. The microcapsular dispersion is cooled to room temperature and mixed with 35 grams of load-bearing material such as Henkel's Keestar-328, a granular, uncooked starch, and 100 grams of a 20% by weight aqueous solution of ethylated starch. The solids of the microcapsular dispersion are adjusted with water to between 35 and 40% by weight.

Two hundred grams of a color developer CF coating prepared according to the procedure of Example 11 are thoroughly mixed with 75 grams of the microcapsular dispersion of this Example, coated onto a paper substrate at a coating weight of about 6.5 gms/m$^2$, and dried. When pressure is applied to the coated surface, the microcapsules are ruptured, releasing the oily material containing the leuco color developers and forming an in-situ black image of high intensity and excellent light stability.

EXAMPLE 29

Examples 1 and 2 are repeated except that the pH is raised to only about 11 to 12. Comparable results are obtained.

EXAMPLE 30

A series of different salicylates and metals were utilized in accordance with the present invention to make CF paper images were formed thereon and tested as to intensity and light resistance. The results are set forth in Table I below. The results show that 100% stoichiometry is not required.

TABLE I

| Salicylate Moiety | % Purity | Metal Compound | % Stoichiom. | Intensity [100-L] | % Light Resistance |
| --- | --- | --- | --- | --- | --- |
| Nonyl SA | 50% | Zn Chloride | 100% | 55.21 | 90.2% |
| Nonyl SA | 50% | Zn Oxide | 100% | 57.10 | 93.1% |
| Nonyl SA | 50% | Zn Oxide | 70% | 56.90 | 93.3% |

TABLE I-continued

| Salicylate Moiety | % Purity | Metal Compound | % Stoichiom. | Intensity [100-L] | % Light Resistance |
|---|---|---|---|---|---|
| Nonyl SA | 50% | Zn Oxide | 150% | 56.00 | 91.0% |
| Nonyl SA | 50% | Li Hydroxide | 90% | 48.50 | 85.5% |
| Nonyl SA | 50% | H (as HCl) | 75% | 55.72 | 90.0% |
| Salicyl. Acid | 100% | Zn Chloride | 100% | 48.00 | 93.0% |
| Salicyl. Acid | 100% | Zn Oxide | 100% | 46.00 | 94.0% |
| Salicyl. Acid | 100% | Zn Octoate | 75% | 44.00 | 90.0% |
| Octyl SA | 100% | Zn Chloride | 100% | 50.00 | 92.5% |
| Octyl SA | 90% | Zn Oxide | 50% | 53.10 | 92.8% |
| Octyl SA | 90% | H (as HCl) | 100% | 56.00 | 84.0% |
| Oligomeric Octyl SA | 71% | Zn Chloride | 88% | 57.30 | 91.5% |
| 3,5 ditert. Butyl SA | 100% | Hydrated Alumina | 50% | 50.00 | 85.4% |
| 3,5 ditert. Butyl SA | 100% | Zn Chloride | 100% | 53.00 | 88.5% |
| 3,5 ditert. Butyl SA | 20% | Zn Oxide | 70% | 55.50 | 88.9% |

EXAMPLE 31

A series of different salicylates and metals were utilized in accordance with the present invention to make CF paper and images were formed therein and tested as to intensity and light resistance. The results are set forth in Table II below. This shows that changing the nature of the pigment and the degree of purity of the salicylates does not adversely affect the properties of the images formed.

TABLE II

| Salicylate Moiety | % Purity | Metal Compound | Extending Pigment | Intensity [100-L] | % Light Resistance |
|---|---|---|---|---|---|
| Nonyl SA | 50% | Zn Oxide | Ca Carbonate | 57.55 | 96.8% |
| Nonyl SA | 50% | Zn Oxide | Kaolin Clays | 56.90 | 94.2% |
| Nonyl SA | 50% | Zn Oxide | Carbonate/Clays | 58.00 | 96.0% |
| Octyl SA | 90% | Zn Oxide | CA Carbonate | 54.56 | 93.2% |
| Octyl SA | 90% | Zn Oxide | Kaolin Clays | 53.80 | 91.1% |
| Octyl SA | 90% | Zn Oxide | Carbonate/Clays | 55.00 | 93.5% |
| Nonyl SA | 100% | Zn Oxide | Kaolin Clays | 53.7 | 87.5% |
| Nonyl SA | 75% | Zn Oxide | Kaolin Clays | 54.3 | 88.0% |
| Nonyl SA | 60% | Zn Oxide | Kaolin Clays | 56.2 | 92.3% |
| Nonyl SA | 50% | Zn Oxide | Kaolin Clays | 57.5 | 92.8% |
| Nonyl SA | 50% | Zn Oxide | Ca Carbonate | 58.0 | 94.8% |
| Nonyl SA | 50% | Zn Chloride | Ca Carbonate | 57.2 | 93.0% |
| Octyl SA | 100% | Zn Oxide | Ca Carbonate | 51.5 | 90.0% |
| Octyl SA | 90% | Zn Oxide | Ca Carbonate | 55.5 | 91.8% |
| 3,5 Ditert. Butyl SA | 100% | Zn Chloride | Ca Carbonate | 53.0 | 88.5% |
| 3,5 Ditert. Butyl SA | 20% | Zn Oxide | Ca Carbonate | 55.8 | 88.9% |

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A pressure-sensitive chromogenic copy system comprising a transfer sheet having on at least a portion of at least one surface thereof a coating of a color developer capable of reacting with a chromogen to form a color image, said color developer comprising the product of combining a hydrogen-donating compound or a metallic compound with an impure reaction mixture from the preparation of a salicylic acid or a salicylate by carboxylation of a phenol, said impure reaction mixture comprising a salicylic component and no less than 10%, by weight of the reaction mixture, of unreacted phenol from said preparation of a salicylic acid or salicylate.

2. The pressure-sensitive chromogenic copy system of claim 1 wherein a hydrogen-donating compound is combined with the impure reaction mixture from the preparation of said salicylic acid or salicylate.

3. The pressure-sensitive chromogenic copy system of claim 1 wherein the metallic compound is lithium or polyvalent metal compound.

4. The pressure-sensitive chromogenic copy system of claims 1, 2, or 3 wherein the color developer contains at least about 1% by weight of salicylate.

5. The pressure-sensitive chromogenic copy system of claim 1, 2, or 3 wherein the pH of said coating is between about 5 and 8.

6. A transfer sheet for a pressure-sensitive chromogenic copy system comprising a substrate having on at least a portion of one surface thereof a coating of a color developer capable of reacting with a chromogen to form a color image, said color developer comprising the product of combining a hydrogen-donating compound or a metallic compound with an impure reaction mixture from the preparation of a salicylic acid or a salicylate by carboxylation of phenol, said impure reaction mixture comprising a salicylic component and no less than 10%, by weight of the reaction mixture, of unreacted phenol from said preparation of a salicylic acid or salicylate.

7. The transfer sheet of claim 6 wherein a hydrogen-donating compound is combined with the impure reaction mixture from the preparation of said salicylic acid or salicylate.

8. The transfer sheet of claim 7 wherein the salicylic acid or salicylate is a $C_{2-12}$ alkyl salicylic acid or salicylate.

9. The transfer sheet of claim 8 wherein the hydrogen donating compound is selected from hydrochloric, acetic, sulfuric, citric, maleic, glyoxylic, or glycolic acid.

10. The transfer sheet of claim 7 wherein said hydrogen donating compound is combined with an impure reaction mixture from the preparation of an octyl or nonyl salicylate.

11. The transfer sheet of claim 6 wherein the metallic compound is a polyvalent metal compound.

12. The transfer sheet of claim 6, 7, or 11 wherein the color developer contains at least about 1% by weight of salicylate.

13. The transfer sheet of claim 6, 7, or 11 wherein the pH of said coating is between about 5 and 8.

14. The transfer sheet of claim 6 wherein the impure reaction mixture has not been subjected to any purification.

15. The transfer sheet of claim 6 wherein the impure reaction mixture is one which has been subjected to partial purification such that the content of the unreacted phenol has been lowered to no less than 20% by weight of the reaction mixture.

16. The transfer sheet of claim 6 wherein the salicylic acid or salicylate is a $C_{2-12}$ alkyl salicylic acid or salicylate.

17. The transfer sheet of claim 16 wherein the hydrogen donating compound is an organic or inorganic acid.

18. The transfer sheet of claim 16 in which the color developer is the product of combining the impure reaction mixture with a lithium compound or a compound of a multivalent metal selected from Groups III A through IV B of the Periodic Table.

19. The transfer sheet of claim 16 in which the color developer is the product of combining the impure reaction mixture with a zinc compound.

20. The transfer sheet of claim 6 in which the color developer is the product of combining the impure reaction mixture with a lithium compound or a compound of a multivalent metal selected from Groups III A through IV B of the Periodic Table.

21. The transfer sheet of claim 6 in which the color developer is the product of combining the impure reaction mixture with a multivalent metal selected from the group consisting of zinc, nickel, cadmium, titanium, aluminum, tin and manganese.

22. The transfer sheet of claim 21 in which the color developer is the product of combining the impure reaction mixture with a multivalent metal compound after adjustment of the pH of said impure reaction mixture to 7.5 to 12.5.

23. The transfer sheet of claim 6 in which the color developer is the product of combining the impure reaction mixture with lithium.

24. A color developer for use in a pressure-sensitive chromogenic copy system, said developer comprising the product of combining a hydrogen-donating compound or a metallic compound with an impure reaction mixture from the preparation of a salicylic acid or salicylate by carboxylation of a phenol, said impure reaction mixture comprising a salicylic component and no less than 10%, by weight of the reaction mixture, of unreacted phenol from said preparation of a salicylic acid or salicylate.

25. The color developer of claim 24 wherein a hydrogen-donating compound is combined with the impure reaction mixture from the preparation of said salicylic acid or salicylate.

26. The color developer of claim 25 wherein the salicylic acid or salicylate is a $C_{2-12}$ alkyl salicylic acid or salicylate.

27. The color developer of claim 26 wherein the hydrogen donating compound is selected from hydrochloric, acetic, sulfuric, citric, maleic, glyoxylic, or glycolic acid.

28. The color developer of claim 25 wherein said hydrogen donating compound is combined with an impure reaction mixture from the preparation of an octyl or nonyl salicylate.

29. The color developer of claim 24 wherein the metallic compound is lithium or polyvalent metal compound.

30. The color developer of claim 29 wherein the color developer contains at least about 1% by weight of salicylate.

31. The color developer of claim 30 wherein the color developer also contains a pigment and a binder.

32. The color developer of claim 24, 25, 29, 30, or 31 wherein said crude reaction medium contains at least about 5% by weight of said salicylate.

33. The color developer of claim 24 wherein the impure reaction mixture has not been subjected to any purification.

34. The color developer of claim 24 wherein the impure reaction mixture is one which has been subjected to partial purification such that the content of the unreacted phenol has been lowered to no less than 20% by weight of the reaction mixture.

35. The color developer of claim 24 wherein the salicylic acid or salicylate is a $C_{2-12}$ alkyl salicylic acid or salicylate.

36. The color developer of claim 35 wherein the hydrogen donating compound is an organic or inorganic acid.

37. The color developer of claim 35 which is the product of combining the impure reaction mixture with a lithium compound or a compound of a multivalent metal selected from Group III A through IV B of the Periodic Table.

38. The color developer of claim 35 which is the product of combining the impure reaction mixture with a zinc compound.

39. The color developer of claim 24 which is the product of combining the impure reaction mixture with a lithium compound or a compound of a multivalent metal selected from Groups III A through IV B of the Periodic Table.

40. The color developer of claim 24 which is the product of combining the impure reaction mixture with a multivalent metal selected from zinc, nickel, cadmium, titanium, aluminum, tin, or manganese.

41. The color developer of claim 40 which is the product of combining the impure reaction mixture with a multivalent metal compound after adjustment of the pH of said impure reaction mixture to 7.5 to 12.5.

42. The color developer of claim 24 which is the product of combining the impure reaction mixture with lithium.

43. A process for the manufacture of a color developer composition for use in a pressure-sensitive chromogenic copy system comprising carboxylating a phenol to form an impure reaction mixture containing a salicylic acid or a salicylate component and at least 10%, by weight of the reaction mixture, of unreacted phenol, forming at least one product of said component by combining said impure reaction mixture with a hydrogen-donating compound or a metallic compound and an effective amount of a binder to form said color developer composition.

44. The process of claim 43 wherein a hydrogen-donating compound is combined with said impure mixture.

45. The process of claim 44 wherein the salicylic acid or salicylate is a $C_{2-12}$ alkyl salicylic acid or salicylate.

46. The process of claim 45 wherein the hydrogen donating compound is selected from hydrochloric, acetic, sulfuric, citric, maleic, glyoxylic, or glycolic acids.

47. The process of claim 44 wherein a hydrogen donating compound is combined with an impure reaction mixture from the preparation of an octyl or nonyl salicylate.

48. The process of claim 43 wherein the metallic compound is lithium or polyvalent metal compound.

49. The process of claim 48 wherein the color developer contains at least about 1% by weight of salicylate.

50. The process of any one of claims 43, 48, or 49 wherein the metallic compound added to form the metal compound of said salicylic compound is zinc oxide or zinc chloride.

51. The process of claim 43, 44, 48, or 49 wherein a pigment is also admixed with said crude reaction medium and said binder in an amount effective to extend the coating surface of said color developer.

52. The process of claim 43, 44, 48, or 49 wherein the pH of said color developer is adjusted such that a dried coating thereof has a pH of about 5 to 8.

53. The process of claim 43 wherein the impure reaction mixture has not been subjected to any purification.

54. The process of claim 43 wherein the impure reaction mixture is one which has been subjected to partial purification such that the content of the unreacted phenol has been lowered to no less than 20% by weight of the reaction mixture.

55. The process of claim 43 wherein the salicylic acid or salicylate is a $C_{2-12}$ alkyl salicylic acid or salicylate.

56. The process of claim 55 wherein the hydrogen donating compound is an organic or inorganic acid.

57. The process of claim 55 which is the product of combining the impure reaction mixture with a lithium compound or a compound of a multivalent metal selected from Group III A through IV B of the Periodic Table.

58. The process of claim 55 which is the product of combining the impure reaction mixture with a zinc compound.

59. The process of claim 43 in which the impure reaction mixture is combined with a lithium compound or a compound of a multivalent metal selected from Group III A through IV B of the Periodic Table.

60. The process of claim 43 in which the impure reaction mixture is combined with a multivalent metal selected from zinc, nickel, cadmium, titanium, aluminum, tin, or magnanese.

61. The process of claim 60 in which the impure reaction mixture is combined with the multivalent metal compound after adjustment of the pH of said impure reaction mixture of 7.5 to 12.5.

62. The process of claim 43 in which the impure product is the product of combining the impure reaction mixture with lithium.

63. A self-contained pressure-sensitive chromogenic copy system comprising at least one sheet having on at least a portion of at least one surface thereof a coating of a color developer comprising the product of combining a hydrogen-donating compound or a metallic compound with an impure reaction mixture from the preparation of a salicylic acid or salicylate by carboxylation of a phenol, said impure reaction mixture comprising a salicylic component and no less than 10%, by weight of the reaction mixture, of unreacted phenol from said preparation of a salicylic acid or salicylate and a chromogen.

64. The self-contained pressure-sensitive chromogenic copy system of claim 63 wherein said color developer and said chromogen are in the same coating.

* * * * *